US00PP29453P2

(12) United States Plant Patent
Van Swieten

(10) Patent No.: US PP29,453 P2
(45) Date of Patent: Jul. 3, 2018

(54) ***PHALAENOPSIS* ORCHID PLANT NAMED 'PHALFOUDI'**

(50) Latin Name: ***Phalaenopsis* hybrid**
Varietal Denomination: PHALFOUDI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/530,890

(22) Filed: Mar. 16, 2017

(51) Int. Cl.
*A01H 5/02* (2018.01)

(52) U.S. Cl.
USPC ..... Plt./311

(58) Field of Classification Search
USPC ..... Plt./311
See application file for complete search history.

(56) References Cited

PUBLICATIONS

UPOV hit on *Phalaenopsis* plant named 'Phalfoudi', QZ PBR 20162203, filed Sep. 13, 2016.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALFOUDI', particularly characterized by having very white flowers, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFOUDI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFOUDI'.

The new *Phalaenopsis* plant is a product of a planned breeding program conducted by the inventor in Bleiswijk, The Netherlands. The objective of this breeding program was to create a new *Phalaenopsis* plant with very white flowers, suitable for potted plant production.

The new *Phalaenopsis* plant 'PHALFOUDI' is a result of cross-pollination made by the inventor in March 2007 in Bleiswijk, The Netherlands of the proprietary female, or seed parent, *Phalaenopsis* hybrid '01-1849' (unpatented) with the proprietary male, or pollen parent, *Phalaenopsis* hybrid '20022-01' (unpatented).

The new *Phalaenopsis* was selected by the inventor as a single plant within the progeny of the stated cross-pollination in a controlled greenhouse in Bleiswijk, The Netherlands in March 2010. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALFOUDI' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFOUDI' as a new and distinct variety of *Phalaenopsis* plant.

1) Very white flowers;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in February 2017. Colors in the photographs may differ from the color values cited in the detailed botanical description, which accurately describe the actual colors of the new variety.

DESCRIPTION OF THE NEW VARIETY

Figure 1:
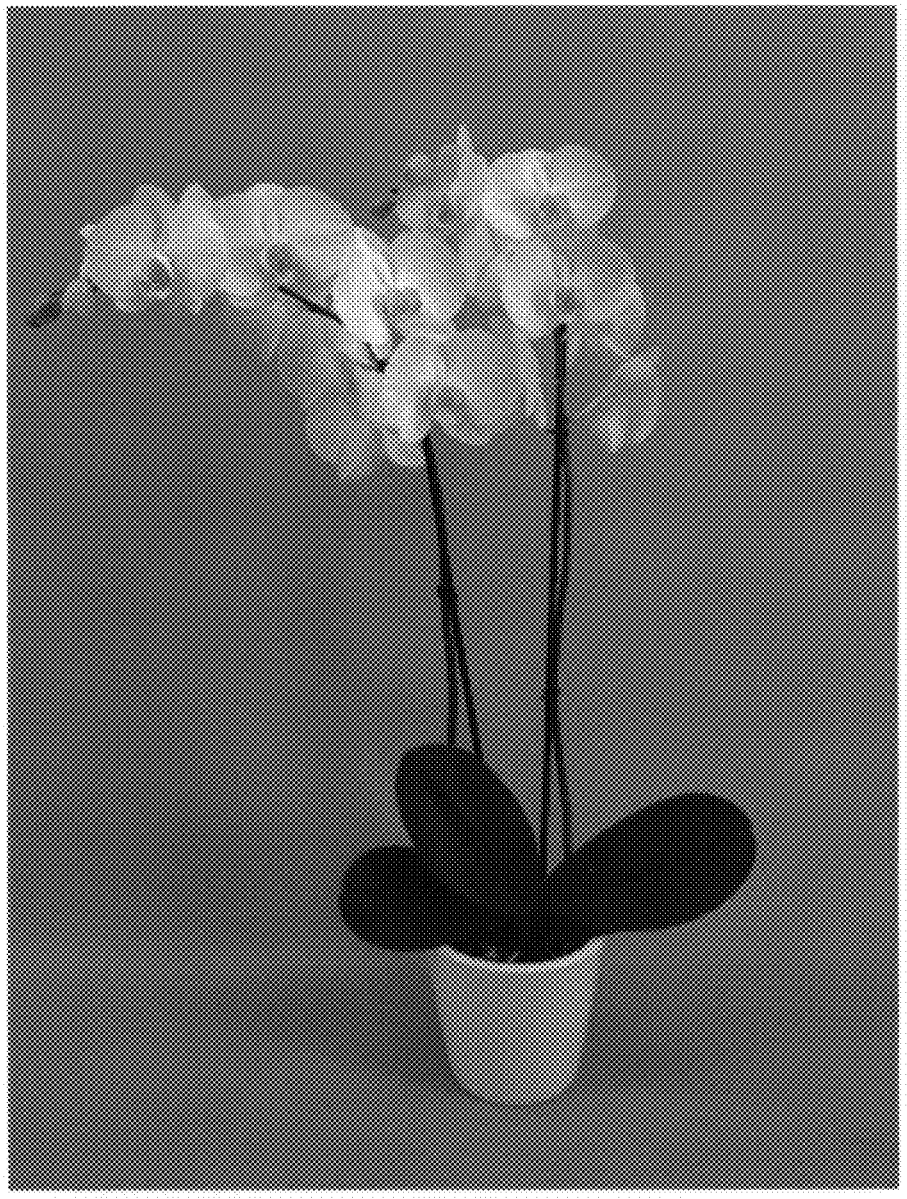
FIG. 1 shows the overall plant habit, including blooms, buds and foliage of 'PHALFOUDI'.
Figure 2:
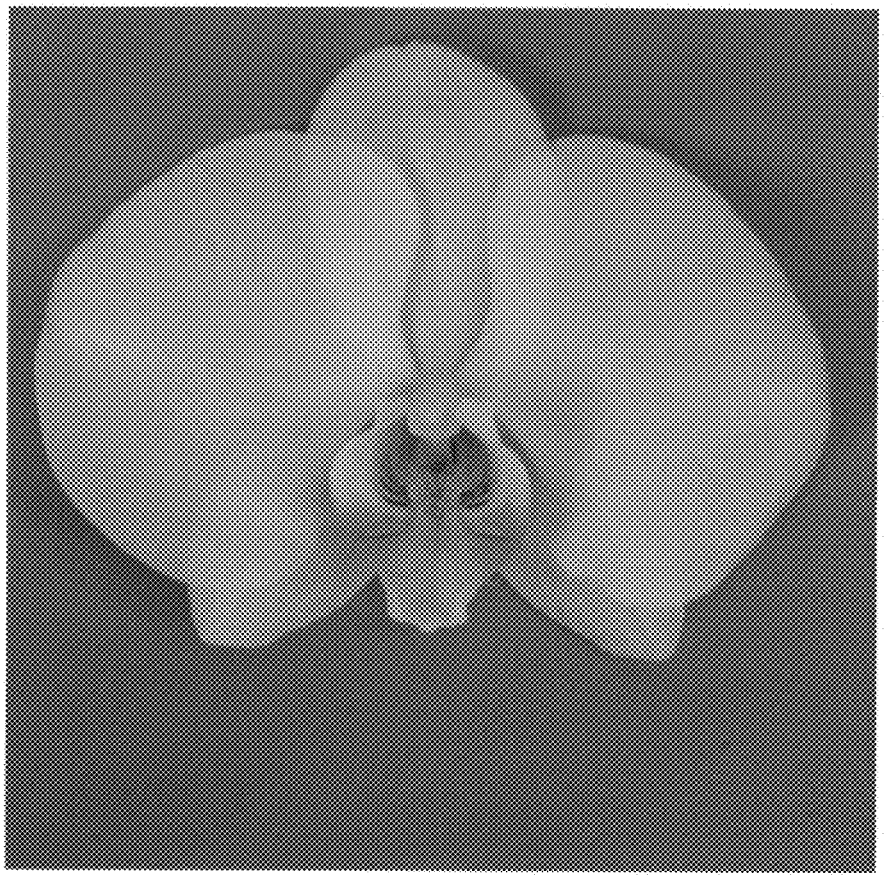
FIG. 2 shows a close-up of a flower of 'PHALFOUDI'.
Figure 3:
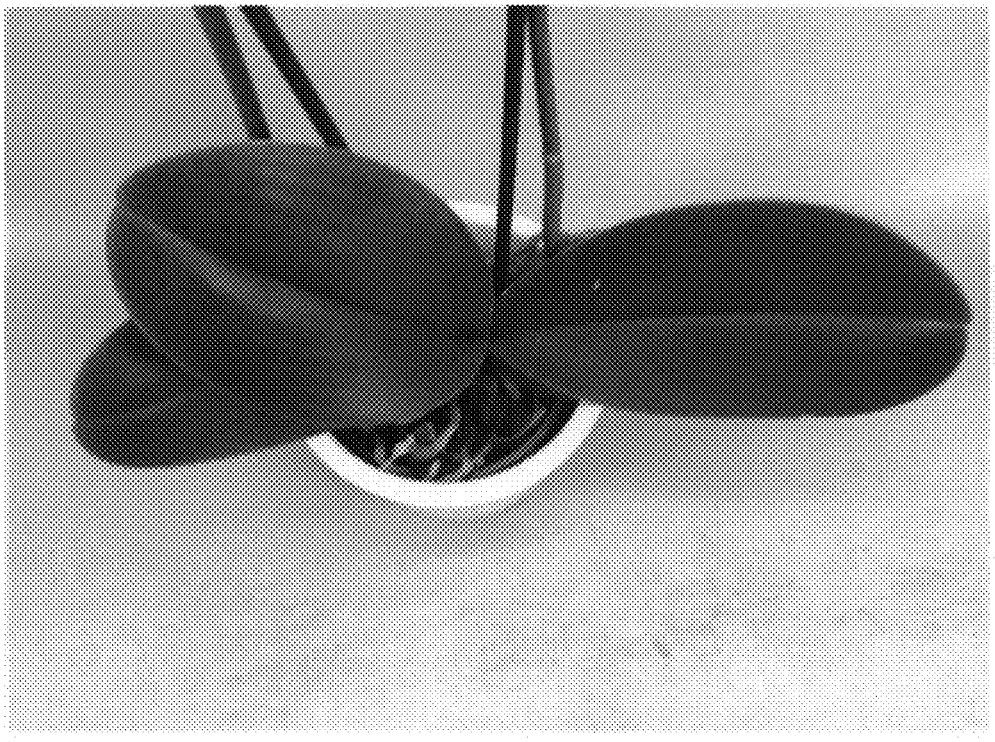
FIG. 3 shows a close-up of the leaves of 'PHALFOUDI'.

The following detailed description sets forth the distinctive characteristics of 'PHALFOUDI'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in February 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFOUDI'.

Parentage:

*Female parent*.—*Phalaenopsis* cultivar '01-1849' (unpatented).

*Male parent*.—*Phalaenopsis* cultivar '20022-01' (unpatented).

Propagation:

*Type*.—Meristem tissue culture.

Roots:

*Root description*.—Greyed-green colored roots (RHS 190B/C) with branching lateral roots having light green colored root tips (RHS 144C).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 65.0 cm to 75.0 cm.

*Width* (*measured from leaf tips*).—About 35.0 cm to 37.0 cm.

*Vigor*.—Strong.

Leaves:

*Mature leaves*.—Quantity per plant: 6 to 8 leaves are produced before flowering. Length (fully expanded): 16.0 cm to 19.0 cm. Width: 9.0 cm to 10.0 cm. Shape: Oblong. Base shape: Moderately elongated. Apex: Rounded. Leaf blade angle with the petiole (measured from the horizontal position): Between 10 degrees and 25 degrees. Leaf margin: Entire. Color: Upper surface: RHS 147A. Lower surface: RHS 147B. Texture: Smooth. Thickness: 2.4 mm to 2.9 mm. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—10 to 14.

*Length*.—65.0 cm to 75.0 cm.

*Diameter*.—6.5 mm to 7.0 mm.

*Strength*.—Strong.

*Aspect*.—Upright to slightly pendant.

*Texture*.—Smooth.

*Color*.—Green (RHS 146A).

*Internode length*.—2.5 cm to 3.0 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 270.0 mm to 300.0 mm.

*Flowering time*.—First flowers can be expected 10 to 11 months after planting in a 12 cm (diameter) pot.

*Flower*.—Height: 83.0 mm to 88.0 mm. Diameter: 100.0 mm to 105.0 mm. Depth of lip: 25.0 mm to 26.0 mm.

*Flower longevity*.—On the plant: 15 to 29 weeks.

*Fragrance*.—Absent.

*Flower bud*.—Average size: Large. Length: 26.0 mm to 28.0 mm. Width: 21.0 mm to 23.0 mm. Shape: Egg shaped. Color: Light green (RHS 145C/D) with diluting light purple regions (RHS 77D).

*Petals*.—Arrangement: Open/free. Shape: Semi-circular. Apex: Rounded asymmetric. Margin: Entire. Length (from base to tip): 45.0 mm to 47.0 mm. Width: 59.0 mm to 61.0 mm. Color (when fully opened): Upper surface: Basic color: White (RHS NN155C). Over color: Absent. Lower surface: Basic color: White (RHS NN155C). Over color: Absent.

*Dorsal sepal*.—Shape: Elliptic. Apex: Emarginated symmetric. Margin: Entire. Length (from base to tip): 45.0 mm to 47.0 mm. Width: 33.0 mm to 35.0 mm. Color (when fully opened): Upper surface: Basic color: White (RHS NN155C). Over color: Absent. Lower surface: Basic color: White (RHS NN155C). Over color: Very light green (RHS 145D) and diluting light purple (RHS 77D).

*Lateral sepals*.—Shape: Ovate. Apex: Obtuse asymmetric. Margin: Entire. Length (from base to tip): 46.0 mm to 48.0 mm. Width: 27.0 mm to 29.0 mm. Color (when fully opened): Upper surface: Basic color: White (RHS NN155C). Over color: Light green at the base (RHS 145D). Lower surface: Basic color: White (RHS NN155C). Over color: Light green (RHS 145D) and slightly light purple toward tips (RHS 77D).

*Labellum* (*lip*).—Whiskers: Present. Length of whiskers: 18.0 mm to 20.0 mm. Color of whiskers: Yellow (RHS 12A). Pubescence on the lip: Absent.

*Lateral lobe*.—Shape: Spatulate. Margin: Undulated. Length: 21.0 mm to 23.0 mm. Width: 16.0 mm to 18.0 mm. Color: White (RHS NN155C) and yellow-green on one side (RHS 5A); with a few stripes and spots at the base (RHS 184A).

*Apical lobe*.—Shape: Triangular. Margin: Entire. Length: 19.0 mm to 21.0 mm. Width: 21.0 mm to 23.0 mm. Color: White (RHS NN155C) and yellow-green at the base (RHS 5A).

*Callus*.—Height: 0.7 cm to 0.8 cm. Length: 0.7 cm to 0.8 cm. Width: 0.4 cm to 0.5 cm. Color: Light yellow (RHS 12A) with very small dots (RHS 174A).

Reproductive organs:

*Column*.—Length: 7.0 mm to 9.0 mm. Diameter: 5.5 mm to 5.9 mm. Color: White (RHS NN155C).

*Pollinia*.—Quantity: 2. Diameter: 1.1 mm to 1.4 mm. Color: Yellow-orange (RHS 25A).

*Ovary*.—Length: 9.0 mm to 11.0 mm. Diameter: 2.5 mm to 2.7 mm.

*Pedicel*.—Length: 42.0 mm to 44.0 mm. Diameter: 2.8 mm to 3.0 mm. Color: Green (RHS 145C) and white (RHS 155C) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND SIMILAR COMMERCIAL VARIETIES

'PHALFOUDI' differs from female parent plant '01-1849' (unpatented) in that 'PHALFOUDI' has larger flowers and shorter whiskers than '01-1849'.

'PHALFOUDI' differs from male parent plant '20022-01' (unpatented) in that 'PHALFOUDI' has a rounded petal apex, whereas '20022-01' has an obtuse petal apex. Additionally, 'PHALFOUDI' has larger flowers and wider petals than '20022-01'.

'PHALFOUDI' is most similar to the commercial *Phalaenopsis* plants named 'PHALCOMWEL' (unpatented) and 'PHALZIFY' (unpatented). 'PHALFOUDI' differs from the commercial variety 'PHALCOMWEL' in that 'PHALFOUDI' has lateral sepals with light green over color, whereas 'PHALCOMWEL' has lateral sepals with no over color. Additionally, 'PHALFOUDI' has taller plants, larger flowers and longer whiskers than 'PHALCOMWEL'.

'PHALFOUDI' differs from the commercial variety 'PHALZIFY' in that 'PHALFOUDI' has lateral sepals with light green over color, whereas 'PHALZIFY' has lateral sepals with no over color. Additionally, 'PHALFOUDI' has taller plants, larger flowers and longer whiskers than 'PHALZIFY'.

I claim:

1. A new and distinct variety of *Phalaenopsis* plant named 'PHALFOUDI', substantially as described and illustrated herein.

* * * * *